(12) United States Patent
Nishida

(10) Patent No.: US 12,263,468 B2
(45) Date of Patent: Apr. 1, 2025

(54) METHOD FOR IMPROVING WATER ABSORPTION OF WATER-ABSORBENT RESIN PARTICLES UNDER LOAD, AND METHOD FOR PRODUCING WATER-ABSORBENT RESIN PARTICLES

(71) Applicant: SUMITOMO SEIKA CHEMICALS CO., LTD., Hyogo (JP)

(72) Inventor: Moe Nishida, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 612 days.

(21) Appl. No.: 17/597,325

(22) PCT Filed: Jul. 1, 2020

(86) PCT No.: PCT/JP2020/025849
§ 371 (c)(1),
(2) Date: Jan. 3, 2022

(87) PCT Pub. No.: WO2021/006153
PCT Pub. Date: Jan. 14, 2021

(65) Prior Publication Data
US 2022/0314200 A1   Oct. 6, 2022

(30) Foreign Application Priority Data
Jul. 5, 2019   (JP) ................. 2019-126335

(51) Int. Cl.
*B01J 20/34*   (2006.01)
*B01J 20/26*   (2006.01)
*B01J 20/28*   (2006.01)
*B01J 20/30*   (2006.01)

(52) U.S. Cl.
CPC ............. *B01J 20/34* (2013.01); *B01J 20/261* (2013.01); *B01J 20/267* (2013.01); *B01J 20/28016* (2013.01)

(58) Field of Classification Search
None
See application file for complete search history.

(56) References Cited

U.S. PATENT DOCUMENTS 5,731,365 A   3/1998 Engelhardt et al.

FOREIGN PATENT DOCUMENTS

| CN | 101808727 | 8/2010 |
| CN | 102648218 | 8/2012 |
| CN | 105593119 | 5/2016 |
| EP | 0812873 B1 | 10/2003 |
| EP | 2190572 A1 | 6/2010 |

(Continued)

OTHER PUBLICATIONS

Yamaden Co., Ltd, "Web page pertaining to a creep meter manufactured by Yamaden Co., Ltd", https://www.ipros.jp/product/detail/print/?objectId=230271&hub=45+bing, Feb. 10, 2005, 4 pages including machine translation.

(Continued)

*Primary Examiner* — Daniel Berns
(74) *Attorney, Agent, or Firm* — HSML P.C.

(57) ABSTRACT

Disclosed is a method for improving a water absorption amount under load by a powder, the method including shaking a powder containing a plurality of water absorbent resin particles while applying a load to the powder. A maximum value of an acceleration received by the powder to be shaken may be 0.050 to 4.0 G.

4 Claims, 3 Drawing Sheets

(56) References Cited

FOREIGN PATENT DOCUMENTS

| | | |
|---|---|---|
| EP | 2263939 | 12/2010 |
| EP | 2190572 B1 | 10/2014 |
| EP | 3031857 | 6/2016 |
| EP | 3053831 | 8/2016 |
| EP | 3202823 A1 | 8/2017 |
| EP | 3312585 | 4/2018 |
| JP | 3103754 B2 | 10/2000 |
| JP | 2002-212301 | 7/2002 |
| JP | 2005-015994 | 1/2005 |
| JP | 2005-015995 | 1/2005 |
| JP | 2006-168324 | 6/2006 |
| JP | 2011-231255 | 11/2011 |
| JP | 2014-094379 | 5/2014 |
| WO | 2009/041731 | 4/2009 |
| WO | 2020/129594 | 6/2020 |

OTHER PUBLICATIONS

Sumitomo Seika, "Super Absorbent Polymer Aqua Keep", Feb. 26, 2001, 2 pages.
International Preliminary Report on Patentability of PCT/JP2020/025849, Jan. 20, 2022, 5 pages.
International Search Report of PCT/JP2020/025849, Sep. 8, 2020, 2 pages.
Office Action issued for Indian Patent Application No. 202247003226, dated Aug. 11, 2023, 6 pages.
The extended European search report of European Patent Application No. 20837118.7, Oct. 17, 2023, 6 pages.

METHOD FOR IMPROVING WATER ABSORPTION OF WATER-ABSORBENT RESIN PARTICLES UNDER LOAD, AND METHOD FOR PRODUCING WATER-ABSORBENT RESIN PARTICLES

TECHNICAL FIELD

The present invention relates to a method for improving a water absorption amount under load by water absorbent resin particles, and a method for producing water absorbent resin particles.

BACKGROUND ART

Water absorbent resin particles are widely used in fields of sanitary materials and the like. It is sometimes necessary that the water absorbent resin particles maintain a large water absorption amount even under load or pressure (for example, Patent Documents 1 and 2).

CITATION LIST

Patent Literature

Patent Document 1: Japanese Unexamined Patent Publication No. 2002-212301
Patent Document 2: Japanese Unexamined Patent Publication No, 2011-231255

SUMMARY OF INVENTION

Technical Problem

An aspect of the present invention provides a method capable of easily improving a water absorption amount under load by water absorbent resin particles.

Solution to Problem

An aspect of the present invention relates to a method for improving a water absorption amount under load by water absorbent resin particles, the method including shaking a powder containing a plurality of water absorbent resin particles while applying a load to the powder.

Another aspect of the present invention relates to a method for producing water absorbent resin particles, the method including improving a water absorption amount under load by water absorbent resin particles by the method described above.

Advantageous Effects of Invention

According to an aspect of the present invention, it is possible to easily improve the water absorption amount under load by the water absorbent resin particles.

DESCRIPTION OF EMBODIMENTS

Hereinafter, some embodiments of the present invention will be described in detail. However, the present invention is not limited to the following embodiments.

In the present specification, "(meth)acryl" means both acryl and methacryl. In the same manner, "acrylate" and "methacrylate" are also referred to as "(meth)acrylate". The same also applies to other similar terms. "(Poly)" means both with and without the prefix "poly". In numerical ranges described stepwise in the present specification, an upper limit value or a lower limit value of a numerical range of one step can be arbitrarily combined with an upper limit value or a lower limit value of a numerical range of another step. In a numerical range described in the present specification, an upper limit value or a lower limit value of the numerical range may be replaced with values shown in examples. "Water-soluble" means that it exhibits a solubility of 5% by mass or more in water at 25° C. The materials exemplified in the present specification may be used alone or in combination of two or more. "Saline solution" refers to a 0.9% by mass sodium chloride aqueous solution.

Figure 1:
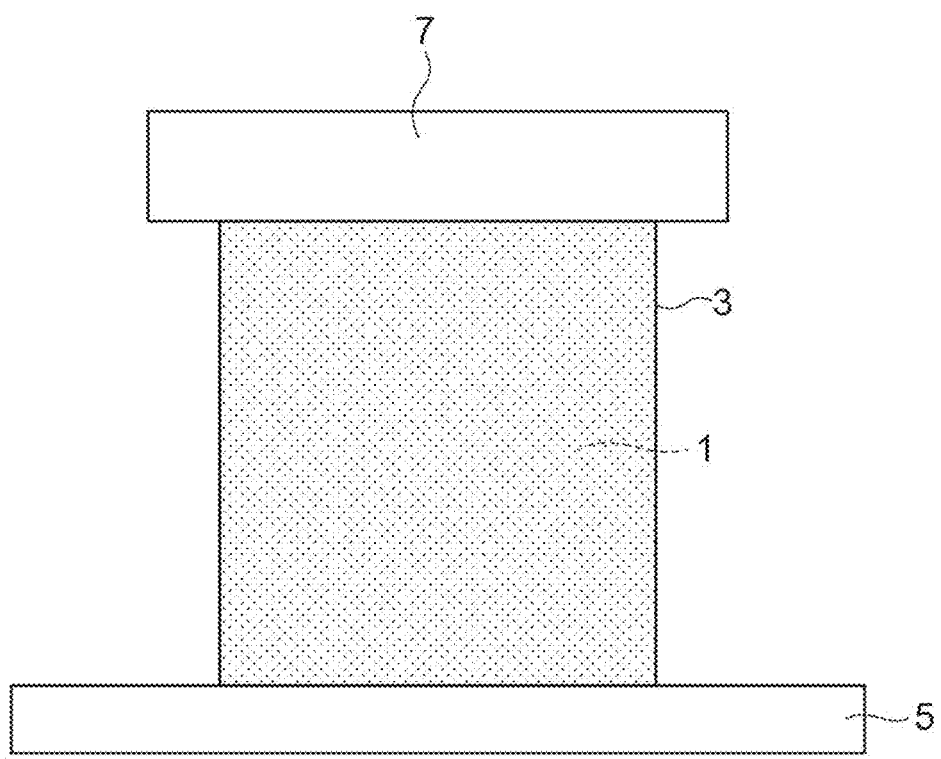
FIG. 1 is a schematic view showing an embodiment of shaking a powder containing water absorbent resin particles.

FIG. 1 is a schematic view showing an embodiment of shaking a powder containing a plurality of water absorbent resin particles. In the method of FIG. 1, a powder 1 contained in a container 3 is shaken. The container 3 is disposed on a support 5, and the powder 1 in the container 3 can be shaken by vibration of the support 5. During the shaking, a load was applied to the entire powder 1 by a weight 7 disposed on an upper portion of the container 3. By shaking the powder 1 while applying the load, water absorbent resin particles showing a larger water absorption amount under load are obtained. The powder 1 is typically configured with substantially only water absorbent resin particles, but other particles may be contained in the powder 1. A rate of the water absorbent resin particles to a total amount of the powder 1 may be 80 to 100% by mass, 90 to 100% by mass, or 95 to 100% by mass.

The container 3 is not particularly limited as long as it can contain the powder 1 and can apply a load to the powder 1. The container 3 may be, for example, a wooden box, a cardboard box, a plastic bag, or a cloth bag. In a case where the container 3 is a flexible bag such as a plastic bag or a cloth bag, the load can be particularly easily applied to the powder 1 by placing the weight 7 on the container 3. The container 3 may have a lid portion that can be opened and closed. In this case, the powder 1 may be shaken in a state where the lid portion is closed, that is, a state where the powder 1 is sealed in the container 3. The powder 1 may be shaken while transporting the container 3 containing the powder 1.

A magnitude of the load applied to the powder 1 by the weight 7 is not particularly limited, and may be, for example, a magnitude so that a pressure of 1.0 to 20.0 kPa is applied to the entire powder 1. In a case where the pressure applied to the powder 1 is within this range, it is possible to particularly effectively improve the water absorption amount under load by the water absorbent resin particles while preventing damage on the water absorbent resin particles constituting the powder 1. From the same viewpoint, the pressure applied to the entire powder 1 may, be 2.5 to 15.0 kPa or 5.0 to 12.0 kPa. For example, in a case where a horizontally projected area of the powder 1 in a state of being contained in the container 3 can be regarded as a working area in which the load by the weight 7 is applied to the powder 1, such as in a case where the container 3 is a flexible bag and the load is applied to the entire powder 1 by the weight 7 placed on the container 3, the pressure can be calculated by the following equation.

Pressure=weight mass/horizontally projected area of powder

A method for applying the load to the powder containing the water absorbent resin particles is not limited to the method for placing the weight on the upper portion of the container. For example, the load may be applied to the powder containing the water absorbent resin particles by a method for stacking another container containing the powder containing the water absorbent resin particles.

The container 3 may be completely filled with the powder 1, or the amount of the powder 1 may be somewhat less than a volume of the container 3, as long as the load can be appropriately applied to the powder 1.

The volume of the container in which the powder containing the water absorbent resin particles is contained for shaking is not particularly limited, and may be, for example, 10 mL to 2000 L. A total mass of the powder to be shaken is not particularly limited, and may be, for example, 10 g to 2000 kg.

A maximum value of an acceleration received by the powder to be shaken may be 0.050 to 4.0 G. In a case where the acceleration is within this range, the water absorption amount under load tends to improve more remarkably. From the same viewpoint, the maximum value of the acceleration may be 0.10 to 3.0 G, 0.30 to 2.5 G, 0.5 to 2.5 G, or 1.0 G to 2.5 G. The maximum value of the acceleration can be calculated based on an amplitude and a frequency of vibration for the shaking.

A time for shaking the powder containing the water absorbent resin particles (shaking time) may be a length that improves the water absorption amount under load by the water absorbent resin particles, and may be, for example, 10 minutes or longer, 20 minutes or longer or 30 minutes or longer, or may be 24 hours or shorter. It is not necessary to continuously shake the powder contained in the container, and the powder may be shaken intermittently while stopping the shaking one or more times in the middle. In a case where the water absorbent resin particles is shaken intermittently, a total shaking time may be within the range described above.

The water absorption amount under load by the water absorbent resin particles after the shaking may be, for example, 15 to 30 g/g. A ratio of the water absorption amount under load by the water absorbent resin particles after the shaking to the water absorption amount under load by the water absorbent resin particles before the shaking may be 103% or more, 105% or more, or 110% or more, and may be 150% or less. The water absorption amount under load here is a value measured by the method described above in examples which will be described later.

The water absorbent resin particles are not particularly limited, and may be particles containing a polymer containing an ethylenically unsaturated monomer as a monomer unit. The ethylenically unsaturated monomer may be a water-soluble monomer, and examples thereof include (meth)acrylic acid and a salt thereof, 2-(meth)acrylamide-2-methylpropanesulfonic acid and a salt thereof, (meth)acrylamide, N,N-dimethyl (meth)acryl amide, 2-hydroxyethyl (meth)acrylate, N-methylol (meth)acrylamide, polyethylene glycol mono(meth)acrylate, N,N-diethylaminoethyl (meth)acrylate, N,N-diethylaminopropyl (meth)acrylate, and diethylaminopropyl (meth)acrylamide. The ethylenically unsaturated monomer may be used alone or in combination of two or more. In a case where the ethylenically unsaturated monomer has a functional group such as a carboxyl group or an amino group, these can function as a functional group for crosslinking the polymer. The water absorbent resin particles may be particles containing a polymer containing at least one of (meth)acrylic acid or a salt of (meth)acrylic acid as a monomer unit.

The polymer constituting the water absorbent resin particles may be a crosslinked polymer. In this case, the polymer may be crosslinked by self-crosslinking, crosslinking by a reaction with a crosslinking agent, or both of them. The water absorbent resin particles may be surface-crosslinked by crosslinking at least the polymer of a surface layer portion thereof with a crosslinking agent. The water absorption amount under load by the surface-crosslinked water absorbent resin particles can be greatly improved by the shaking. The crosslinking agent for the surface crosslinking may be referred to as a surface crosslinking agent.

Examples of the crosslinking agent include polyols such as ethylene glycol, propylene glycol, 1,4-butanediol, trimethylolpropane, glycerin, polyoxyethylene glycol, polyoxypropylene glycol, and polyglycerin; compounds having two or more epoxy groups such as (poly)ethylene glycol diglycidyl ether, (poly)propylene glycol diglycidyl ether, and (poly)glycerin diglycidyl ether; haloepoxide compounds such as epichlorohydrin, epibromhydrin, and α-methylepichlorohydrin, compounds having two or more isocyanate groups such as 2,4-tolylene diisocyanate and hexamethylene diisocyanate; oxazoline compounds such as 1,2-ethylene bisoxazoline; carbonate compounds such as ethylene carbonate; and hydroxyalkylamide compounds such as bis[N,N-di(β-hydroxyethyl)]adipamide. The crosslinking agent may contain a polyglycidyl compound such as (poly)ethylene glycol diglycidyl ether, (poly)glycerin diglycidyl ether, (poly)glycerin triglycidyl ether, (poly)propylene glycol polyglycidyl ether, and polyglycerol polyglycidyl ether. These crosslinking agents may be used alone or in combination of two or more.

The water absorbent resin particles may contain various additional components, in addition to the polymer of the ethylenically unsaturated monomer. Examples of additional components include a gel stabilizer, a metal chelating agent, and a flowability improving agent (lubricant). The additional components may be disposed inside the polymer particles containing the polymer, on surfaces of the polymer particles, or both of them. The additional component may be a flowability improving agent (lubricant). The flowability improving agent may contain inorganic particles. Examples of the inorganic particles include silica particles such as amorphous silica.

A shape of the water absorbent resin particles is not particularly limited, and may be, for example, a substantially spherical shape, a crushed shape, or a granular shape, and particles obtained by aggregating primary particles having these shapes may be formed. A median particle size of the water absorbent resin particles may be 250 to 850 μm, 300 to 700 μm, or 300 to 600 μm.

The water absorbent resin particles can be, for example, produced by a method including obtaining water absorbent resin particles containing a polymer containing an ethylenically unsaturated monomer as a monomer unit by a method including polymerizing a monomer containing an ethylenically unsaturated monomer, and improving the water absorption amount under load by the water absorbent resin particles by the method according to the embodiment described above. The monomer polymerization method can be selected from, for example, a reverse phase suspension polymerization method, an aqueous solution polymerization method, a bulk polymerization method, and a precipitation polymerization method, From viewpoints of ensuring better water absorption characteristics of the water absorbent resin particles and easily controlling a polymerization reaction, the reverse phase suspension polymerization method or the aqueous solution polymerization method may be used. If necessary, formation of particles by a crosslinking reaction during or after the polymerization, or pulverization, drying, and the like can be performed by a general method. The surface-crosslinked water absorbent resin particles can be obtained by a reaction between the particles after the polymerization and the drying and the surface crosslinking agent.

Various absorbent products such as diapers can be produced by using the water absorbent resin particles having an improved water absorption amount under load.

EXAMPLES

Hereinafter, the present invention will be described in more detail with reference to examples. However, the present invention is not limited to these examples.

1. Measurement Method 1-1. Tapped Bulk Density of Powder Consisting of Water Absorbent Resin Particles The tapped bulk density of the powder consisting of water absorbent resin particles was measured with a powder property evaluation device (manufactured by Hosokawa Micron Corporation, model number: PT-X) by the following procedure. The tapped bulk density was measured under conditions of room temperature (25° C.±2° C.) and humidity of 50%±10%.

A mass W0 of a cup-shaped container (volume of 100 mL, inner diameter of approximately 50 mm, height of approximately 50 mm) in an empty state was measured. Next, a cylindrical cap (inner diameter of 51 mm, height of 51 mm) was attached to an upper portion of the container. Through an upper opening of the cap, 100 g of powder was put into a container with a scoop attached to a device. Subsequently, the container was placed on a tapping lift bar (tapping device), and the powder in the container was impacted by tapping 180 times with a stroke of 18 mm. Then, after removing the cap, the powder in a portion raised from the upper opening of the container was removed by scraping with a blade. Subsequently, a mass W1 of the container containing the powder was measured. Based on the mass W0 and the mass W1, the tapped bulk density was obtained by the following equation. The tapped bulk density was measured three times in total, and an average value thereof was recorded as the tapped bulk density D [g/mL] of the powder consisting of water absorbent resin particles.

Tapped bulk density [g/mL]=($W1$[g]−$W0$[g])/100 [mL]

1-2. Theoretical Filling Rate

The theoretical filling rate in a case where the powder consisting of water absorbent resin particles was put into a polyethylene bag with a zipper was obtained by the following equation.

Theoretical filling rate [%]={($X$[g]/$D$[g/ML])/$V$ [mL]}×100

In the equation, X represents a mass of the powder, D represents a tapped bulk density of the powder, and V represents a volume of a polyethylene bag. A volume of a maximum amount of pure water that can be filled in the polyethylene bag with the zipper closed was measured, and this was defined as the maximum capacity of the polyethylene bag.

1-3. Water Absorption Amount Under Load (Load: 4.14 kPa)

Figure 2:
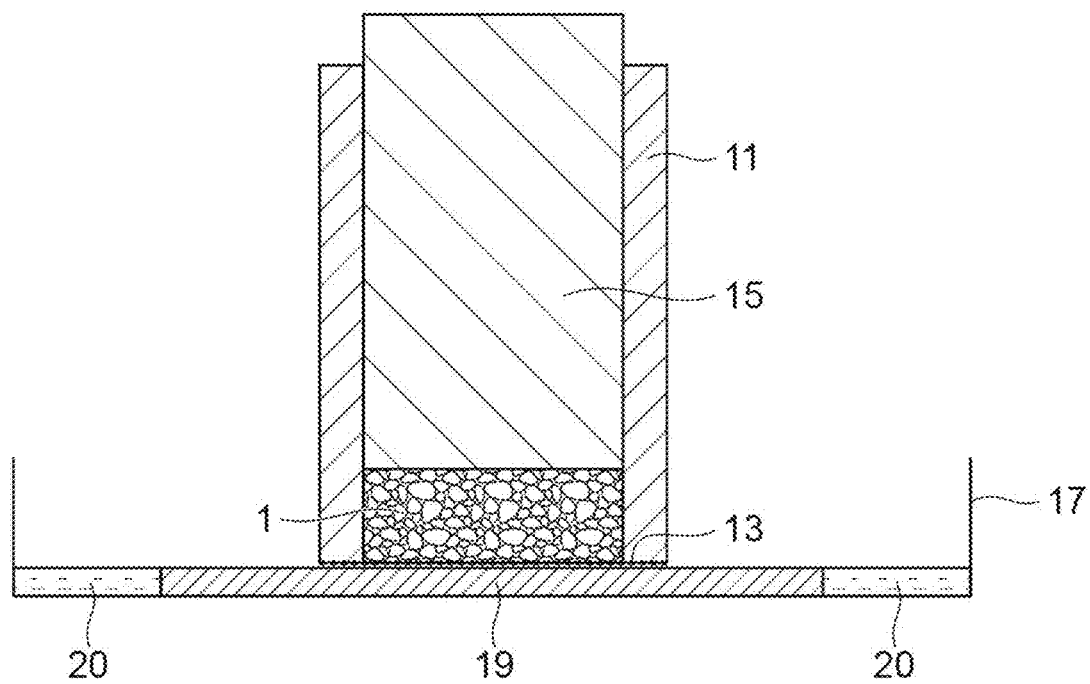
FIG. 2 is a schematic view showing a method of measuring a water absorption amount under load by the water absorbent resin particles.

The water absorption amount under load was measured under conditions of room temperature (25° C.±2° C.) and humidity of 50%±10%. FIG. 2 is a schematic view showing a method for measuring the water absorption amount under load. A glass filter 19 (diameter of 9 cm, thickness of 7 mm, standard: ISO4793, P-250) was placed in a petri dish 17 having an inner diameter of 12 cm. Next, a saline solution 20 was put into the petri dish 17 to a height of the glass filter 19. The powder 1 consisting of the water absorbent resin particles having the mass X [g] was evenly put into a cylinder 11 (inner diameter of 2.0 cm: outer diameter of 3.0 cm: height of 5.0 cm) in which a 255 mesh bolting cloth (nylon mesh) 13 is mounted on an end portion. Here, X was 0.1000±0.0005 g. On the powder 1 in the cylinder, a cylindrical weight 15 having a mass for applying a pressure of 4.14 kPa to the powder 1 was placed. The weight 15 has an outer diameter slightly smaller than the inner diameter of the cylinder, and can smoothly move in a vertical direction in the cylinder. In this state, the total mass W1 [g] (total mass of the powder 1, the cylinder 11, the bolting cloth 13, and the weight 15) was measured. The cylinder 11 containing the powder 1 and the weight 15 was placed on the glass filter 19 in the petri dish 17, and the powder 1 was swollen with the saline solution 20 for 1 hour. A total mass W2 [g] of the swelled powder 1, the cylinder 11, the bolting cloth 13, and the weight 15 was measured. A loss on drying A [%] of the powder consisting of the water absorbent resin particles was also separately measured by the method which will be described later. The water absorption amount under load was calculated by the following equation.

Water absorption amount under load[g/g]=($W2$−$W1$)/ {$X$×100−$A$)/100}

The water absorption amount under load was measured five times, and an average value of the Obtained measured values was recorded as the water absorption amount under load by the water absorbent resin particles. According to this method, the water absorption amount under load is measured by removing an effect of the change in loss on drying on the measured value. Therefore, even in a case where the loss on drying increases or decreases, a numerical value of the water absorption amount under load can be compared.

1-4. Loss on Drying 2.0 g of powder consisting of water absorbent resin particles was placed on an aluminum wheel case (No. 8) having a constant amount (W3 (g)) in advance, and a mass W4 (g) thereof was precisely weighed. The precisely weighed powder was dried for 2 hours in a hot air dryer (manufactured by ADVANTEC, model: FV-320) whose internal temperature was set to 105° C. After allowing the powder to cool in a desiccator, a mass W5 (g) thereof was measured as a dry mass. The loss on drying of the water absorbent resin particles was calculated from the following equation.

Loss on drying (% by mass)=[{($W4$−$W3$)− (($W5$−$W3$)}/($W4$−$W3$)]×100

2. Water Absorbent Resin Particles

Aquakeep SA60SXII (trade name, particles containing sodium polyacrylate) manufactured by Sumitomo Seika Chemicals Co., Ltd. was prepared as the water absorbent resin particles. The tapped bulk density of the powder consisting of the water absorbent resin particles was 0.83 g/mL.

3. Shaking Test

The powder consisting of water absorbent resin particles was filled in a polyethylene bag with a zipper (size inside the zipper: 70 mm×50 mm, thickness of 0.04 mm, volume of 35 mL). The amount of powder to be filled was 29.05 g, which was an amount corresponding to a theoretical filling rate of 100%.

A polyethylene bag filled with powder was placed on a saucer for JIS Z8801 with the zipper portion located sideways. A 1.0 kg, 2.0 kg, 3.5 kg, or 5.0 kg weight (bottom surface: 10×10 cm) was placed on the polyethylene bag placed on the saucer, and the weight was fixed to the polyethylene bag with an adhesive tape. The horizontally projected area of the polyethylene bag placed on the saucer was regarded as a working area where the load was applied to the powder from the weight, and a pressure applied to the entire powder of the water absorbent resin particles was estimated by the following equation.

$$\text{Pressure [kPa]} = \text{weight mass[kg]}/3500[\text{mm}^2] \times 9.81 \times 10^3$$

Next, the powder was shaken for 30 minutes or 300 minutes by applying vibration containing vertical motion to the saucer for 30 minutes by using an electromagnetic vibration type sieve shaker Octagon 200 (manufactured by endecotts) with a vibration strength set to 1 or 7. A calculated value of the acceleration received by the powder is 0.1 G at the maximum in a case where the vibration strength is 1, and 2.2 G at the maximum in a case where the vibration strength is 7. The water absorption amount under load by the water absorbent resin particles after the shaking was measured. For the comparison, the water absorption amount under load by the water absorbent resin particles before the shaking was also measured.

TABLE 1

| | Vibration strength | Acceleration | Shaking time [minutes] | Weight mass [kg] | Pressure [kPa] | Loss on drying [%] | Water absorption amount under load [g/g] |
|---|---|---|---|---|---|---|---|
| Before shaking | — | — | — | — | 0 | 9.7 | 17.4 |
| Ex. 1 | 1 | 0.1 G | 30 | 5.0 | 14.01 | 9.2 | 17.9 |
| Ex. 2 | 1 | 0.1 G | 30 | 3.5 | 9.81 | 9.3 | 18.6 |
| Ex. 3 | 1 | 0.1 G | 30 | 2.0 | 5.60 | 9.7 | 18.2 |
| Ex. 4 | 1 | 0.1 G | 30 | 1.0 | 2.80 | 9.6 | 18.0 |
| Comp. Ex. 1 | 1 | 0.1 G | 30 | 0 | 0 | 9.5 | 17.8 |
| Ex. 5 | 7 | 2.2 G | 30 | 5.0 | 14.01 | 9.7 | 18.3 |
| Ex. 6 | 7 | 2.2 G | 30 | 3.5 | 9.81 | 10.2 | 20.4 |
| Ex. 7 | 7 | 2.2 G | 30 | 2.0 | 5.60 | 9.7 | 19.4 |
| Ex. 8 | 7 | 2.2 G | 30 | 1.0 | 2.80 | 9.5 | 18.4 |
| Comp. Ex. 2 | 7 | 2.2 G | 30 | 0 | 0 | 9.5 | 18.2 |
| Ex. 9 | 7 | 2.2 G | 300 | 3.5 | 9.81 | 9.7 | 19.3 |

Figure 3:
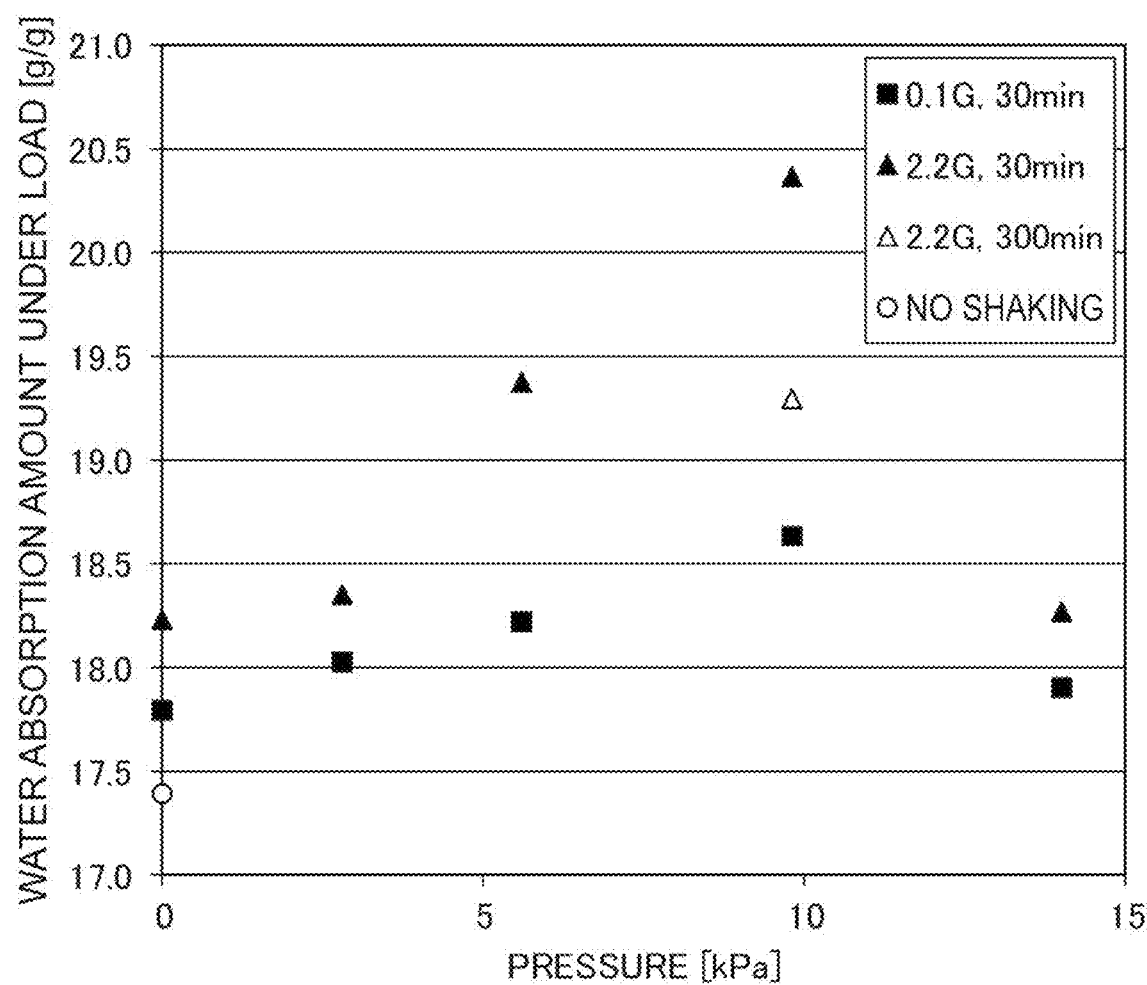
FIG. 3 is a graph showing a relationship between the water absorption amount under load and a pressure applied to the powder containing water absorbent resin particles.

Table 1 shows measurement results of the water absorption amount under load. FIG. 3 is a graph showing a relationship between the water absorption amount under load and a pressure applied to the powder. It was confirmed that, by shaking the powder of the water absorbent resin particles in a state where the load is applied, the water absorption amount under load was clearly improved as compared with that before the shaking.

REFERENCE SIGNS LIST

1: Powder containing water absorbent resin particles
3: Container
5: Support
7: Weight

The invention claimed is:

1. A method for improving a water absorption amount under load by water absorbent resin particles, the method comprising:
    shaking a powder containing a plurality of water absorbent resin particles while applying a load to the powder, the application of the load to the powder resulting in a pressure of 1.0 to 20.0 kPa being applied to an entirety of the powder.

2. The method according to claim 1, wherein a maximum value of an acceleration received by the powder during shaking is 0.050 to 4.0 G.

3. The method according to claim 1, wherein a time for shaking the powder is 10 minutes or longer in total.

4. A method for producing water absorbent resin particles, the method comprising:
    improving a water absorption amount under load by water absorbent resin particles by the method according to claim 1.

* * * * *